United States Patent
Ray

(10) Patent No.: US 8,172,783 B1
(45) Date of Patent: May 8, 2012

(54) CONDUIT SYSTEM FOR ISOLATION OF FLUIDS IN BIOLOGICAL TISSUES

(75) Inventor: Pinaki Ray, Fremont, CA (US)

(73) Assignee: Advanced Cardiovascular Systems, Inc, Santa Clara, CA (US)

( * ) Notice: Subject to any disclaimer, the term of this patent is extended or adjusted under 35 U.S.C. 154(b) by 1826 days.

(21) Appl. No.: 09/475,768

(22) Filed: Dec. 30, 1999

(51) Int. Cl.
*A61M 37/00* (2006.01)

(52) U.S. Cl. .......... 604/4.01; 604/8; 604/9; 604/103.03; 604/284

(58) Field of Classification Search .................. 604/4.01, 604/5.01–5.04, 6.01–6.16, 8–9, 506–509, 604/93.01, 96.01, 97.01–97.03, 98.01–98.02, 604/99.01–99.03, 103.3, 173, 264, 523, 532, 604/284, 103.01

See application file for complete search history.

(56) References Cited

U.S. PATENT DOCUMENTS

| | | | |
|---|---|---|---|
| 4,192,302 A * | 3/1980 | Boddie ........................ 604/5.04 |
| 4,540,402 A * | 9/1985 | Aigner ............................ 604/44 |
| 4,994,033 A | 2/1991 | Shockey et al. |
| 5,002,528 A | 3/1991 | Palestrant |
| 5,102,402 A | 4/1992 | Dror et al. |
| 5,180,366 A | 1/1993 | Woods |
| 5,304,121 A | 4/1994 | Sahatjian |
| 5,324,261 A | 6/1994 | Amundson et al. |
| 5,370,610 A | 12/1994 | Reynolds |
| 5,370,614 A | 12/1994 | Amundson et al. |
| 5,380,307 A | 1/1995 | Chee et al. |
| 5,397,307 A | 3/1995 | Goodin |
| 5,415,636 A | 5/1995 | Forman |
| 5,452,733 A * | 9/1995 | Sterman et al. ................ 128/898 |
| 5,462,523 A | 10/1995 | Samson et al. |
| 5,478,309 A * | 12/1995 | Sweezer et al. .......... 604/101.04 |
| 5,514,092 A | 5/1996 | Forman et al. |
| 5,538,504 A | 7/1996 | Linden et al. |
| 5,554,119 A | 9/1996 | Harrison et al. |
| 5,558,642 A | 9/1996 | Schweich, Jr. et al. |
| 5,588,962 A | 12/1996 | Nicholas et al. |
| 5,674,192 A | 10/1997 | Sahatjian et al. |
| 5,725,496 A | 3/1998 | Peters |
| 5,725,796 A | 3/1998 | Finkenzeller et al. |
| 5,772,632 A | 6/1998 | Forman |
| 5,792,094 A | 8/1998 | Stevens et al. |
| 5,792,095 A | 8/1998 | Kissinger et al. |
| 5,792,105 A | 8/1998 | Lin et al. |

(Continued)

OTHER PUBLICATIONS

Y. Akamo, et al., "Chemotherapy Targeting Regional Lymph Nodes by Gastric Submucosal Injection of Liposomal Adriamycin in Patients with Gastric Carcinoma," Jpn. J. Cancer Research, Jun. 1994, pp. 652-658, vol. 85.

(Continued)

*Primary Examiner* — Laura Bouchelle
(74) *Attorney, Agent, or Firm* — Blakely, Sokoloff, Taylor & Zafman, LLP

(57) ABSTRACT

The invention presents is a fluid isolation system and method for confining fluid is a biological mass having at least one upstream channel and downstream channel. The system includes a delivery conduit for administering fluid to the biological mass and a collection conduit having and external seal and for retrieving the fluid. In the use of the system, the delivery conduit is positioned adjacent to or into the upstream channel and the collection conduit is inserted adjacent to or into the downstream channel. In one manner to confine the fluid, the seal on the collection catheter is activated to occlude outside fluid flow and divert the fluid into the lumen of the catheter.

30 Claims, 7 Drawing Sheets

U.S. PATENT DOCUMENTS

| | | | |
|---|---|---|---|
| 5,795,318 A | | 8/1998 | Wang et al. |
| 5,797,870 A | | 8/1998 | March et al. |
| 5,817,046 A | * | 10/1998 | Glickman .................... 604/158 |
| 5,843,033 A | | 12/1998 | Ropiak |
| 5,860,954 A | | 1/1999 | Ropiak |
| 5,866,561 A | | 2/1999 | Ungs |
| 5,868,719 A | | 2/1999 | Tsukenik |
| 5,893,840 A | | 4/1999 | Hull et al. |
| 5,951,458 A | | 9/1999 | Hastings et al. |
| 5,954,706 A | | 9/1999 | Sahatjian |
| 6,013,099 A | | 1/2000 | Dinh et al. |
| 6,059,814 A | | 5/2000 | Ladd |
| 6,068,645 A | | 5/2000 | Tu |

OTHER PUBLICATIONS

E. Nabel, et al., "Safety and Toxicity of Catheter Gene Delivery to the Pulmonary Vasculature in a Patient with Metastatic Melanoma," Human Gene Therapy, Sep. 1994, pp. 1089-1094, vol. 5.

D. August, et al., "Pharmacokinetic Evaluation of Percuatneous Hepatic Venous Isolation for Administration of Regional Chemotherapy," Surgical Oncology, 1995, pp. 205-216, vol. 4.

I. Raad, et al., "Silver Iontophoretic Catheter: A Prototype of a Long-Term Antiinfective Vascular Access Device," The Journal of Infectious Diseases, Feb. 1996, pp. 495-498, vol. 173:2.

H. Ohigashi M.D., et al., "A New Method of Intra-Arterial Regional Chemotherapy With More Selective Drug Delivery for Locally Advanced Pancreatic Cancer" Hepato-Gastroenterology, Mar.-Apr. 1996, pp. 338-345, vol. 43.

E. Tan, et al., "5-Fluorouracil Continuous Infusion in Metastatic Colorectal Cancer," Annals Academy of Medicine, Sep. 1996, pp. 748-751, vol. 25:5.

D. Stephan, et al., "A New Cationic Liposome DNA Complex Enhances the Efficiency of Arterial Gene Transfer In Vivo," Human Gene Therapy, Oct. 1996, pp. 1803-1812, vol. 7.

S. Bailey, "Local Drug Delivery: Current Applications," Progress in Cardiovascular Diseases, Sep./Oct. 1997.

R. Fasol PD, et al., "Coronary Artery Angiogenesis Induced by Surgically Implanted Growth Factor: Clinical Results After One Year," ESC Press Release (http://www.escardio.org/index.htm), Aug. 22-26, 1998, Germany.

* cited by examiner

CONDUIT SYSTEM FOR ISOLATION OF FLUIDS IN BIOLOGICAL TISSUES

FIELD OF THE INVENTION

The present invention relates generally to the isolation of fluids in a biological system, and more particularly to a conduit platform for delivery and collection of a fluid at a target site.

BACKGROUND

Medical and veterinary diagnosis, therapy and disease prevention often involve the introduction of chemicals to alter the body's function at the molecular level. Advancements in treatment procedures and pharmaceutical development have expanded the scope of available chemical agents. The types of agents that are administered to biological systems include growth factors, gene therapy compositions, chemotherapeutic agents, anti-bacterial agents, a wide variety of natural and synthetic drugs, and the like.

Agent efficacy is a major consideration in the selection of such chemicals. In particular, the practical utility of the agent is significantly impacted by subordinate effects, referred to as side effects, which are produced by an agent in addition to the agent's primary intended function. Such secondary results may be caused by an agent's ability to bind to more than one species of receptor. The exposure of the agent to various receptors produces a range of physiological responses. Side effect may also occur because receptors attach to different types of cells that control various biochemical processes. Consequently, agents that contact multiple receptor sites inside of a biological system may induce an assortment of clinical effects.

Another factor influencing the efficacy of a chemical agent is the agent's ability to produce the intended effect at sites of the body in addition to the target tissue, referred to as decentralized effects. Frequently, it is desirable for the chemical to provide only localized treatment, such as to an injured area or to a surgical site. For example, operations are often accompanied by treatment with heparin to prevent blood clotting at the site of surgery. However, dispersion of heparin to other sites may cause hemorrhaging throughout the body.

Where decentralized effects and side effects caused by an agent are deleterious to the body, the agent's usefulness is limited. Often, the trade-off between benefits and toxicity means a potentially helpful agent can not be employed for therapy due to the undesirable effects that occur as the agent passes through the body. Furthermore, often a less than optimal dosage of agent must be used in order to lessen these undesirable effects. Thus, it is often not possible to conduct treatments with high concentrations of toxic agents and to repeatedly expose the body to drugs for long-term treatments.

The occurrence of undesirable effects is significantly impacted by the agent's route of administration, travel between different parts of the body and excretion from the target site. Routes of administration include intravenous, oral, inhalational, topical, transdermal, subcutaneous, intramuscular, buccal, intra-arterial, intrathecal and rectal. Methods of directly administering are highly beneficial. Such local applications allow a higher bioavailablity of the chemical at the target site. Where the agent must travel extensively through the body to reach the target tissue, the agent may be metabolized in the gut, portal blood or liver prior to entry into other systemic circulation. Moreover, an agent traveling through the circulation to reach its proposed destination may be retained by blood plasma proteins instead of binding to its intended tissue protein. Direct routes are also useful for reducing potential undesirable effects, producing high local concentrations of agent at the treatment site, and continuously attending to chronic conditions.

Special routes of administration are available for dispensing agents directly to a target tissue. The agents may be attached to a carrier that is implanted near the target site, i.e. drug delivery stents. Other local agent delivery devices include microporous balloon catheters, intravascular injection catheters, ultrasound enhanced delivery through microporous balloon catheters, etc. Intra-vascular, intraoperative or intrathecal catheters may also be surgically inserted near the target organ for delivery of agents. In an exemplary case, gene therapy agents are presented to the heart through a catheter that is percutaneously introduced, such as through the femoral artery, and guided upstream into the coronary artery for agent introduction into the perivascular space. Alternatively, the agent is introduced into the left ventricle and epicardium for agent introduction into the pericardial space. In such procedures, access to the pericardium may also be gained intra-vascular or through a thoracotomy.

However, many of the delivery devices mentioned above are not appropriate for prolonged drug delivery, i.e. longer than a few minutes, because they block the flow of blood. Continuous drug delivery over a long period of time may permit increased depth of penetration of the agent into the target site. For example, it is observed that an artery soaked overnight in a dye absorbs the dye through the thickness of the artery to the outer most vessel layer. Where a delivery device must be repeatedly inserted into a treatment site, damage to the vessel walls by the device may occur with each entrance. Furthermore, the repetitive use of traditional stiff porous balloons to deliver fluid has tendency to cause additional damage to the vessel. These porous balloon catheters need a great deal of pressure to stretch the vessel and deliver the drug, often resulting in vessel injury at the contact site. Frequently, shorter treatment times are imposed in attempts to limit damage to the tissue as well as minimize the exposure of other parts of the body to potentially toxic effects. Thus, it is beneficial for delivery devices to permit long-term treatment without repeatedly injuring the body.

It is also advantageous for devices to control the passage of chemicals from the target site to undesirable paths in the body. Where the tissue is exposed to an agent, it is useful to prevent dissemination of the chemical to the other circulatory paths. For example, agents administered to the heart should be prevented from traveling to the systemic circulation. Many of these agents are toxic to the remainder of the body.

Methods of compartmentalizing a chemical within a target site are important for improving an agent's effectiveness and permitting long-term treatment. Many medical procedures are greatly facilitated by techniques for isolating an agent's area of contact. Coronary heart disease, for example, is the most common disease and cause of death in developed nations. In the treatment of atheroslerotic coronary disease, percutaneous transluminal coronary angioplasty (PTCA) may be performed to reduce obstructions in a vessel. PTCA involves the introduction of a catheter with a small dilating balloon at its tip. The catheter is maneuvered through the arteries, often in the arm or leg, to a site in a coronary artery where the vessel has narrowed. The balloon is inflated to increase the cross-sectional area of the vessel.

Although PTCA treatment has a high success rate in widening the vessel, the vessel may re-narrow or re-close afterwards, referred to as "restenosis." Treatment of restenosis includes delivery of anti-proliferative drugs to the site of the diseased area following PTCA and during the same surgery.

Yet, the drug treatment is only mildly effective due to many factors, including the amount of drug that is absorbed by the cells and diffusion of the drug out of the tissue and back into the coronary circulation. Removal of the drug by the blood stream may take place quicker than the time it takes for the onset of restenosis.

In order to address these problems with restenosis treatment and other therapies, it is necessary to administer high concentrations of therapeutic agents over long periods of time. Such intense drug therapy is only possible if the drug is applied exclusively to the target site.

In another example of agent delivery, growth factors, such as basic fibroblast growth factor, are being applied to the heart muscle in the treatment of advanced coronary artery obstructive disease. Growth factor may induce coronary angiogenesis and new coronary collateral blood vessel growth. However, growth factors function indiscriminately to initiate the growth of new vascular structures and may be undesirable to other areas of the body. A problematic aspect of the treatment involves the agent's potential ability to facilitate growth of benign cancerous tumors located outside of the agent's target area. It is essential that the growth factor be applied specifically to the heart and be isolated from other tissues of the body.

In addition, gene therapy agents are widely used for transferring genetic information to certain cells. Gene transfer involves the delivery to target cells of one or more genes along with the sequences for controlling their expression that are embedded within a vector system. Human gene transfer can be done in vivo by viral transduction and physical transfection. It is desirable that the genetic material is maintained at the area of interest for optimal cell targeting.

Some conditions involve many dispersed damaged sites. Indiscrete stenosis, i.e. an obstruction to forward blood flow in the heart, may be represented by numerous lesion sites within several coronary vessels. It is impractical to treat indiscrete stenosis with conventional PCTA because the balloons need to contact each focal lesion and individually open each occluded site. There are risks of vessel damage to insert multiple balloons at many sites. Perfusing the heart with therapeutic drugs may treat indiscrete stenosis. Procedures to perfuse such arteries having multiple occlusions with agent yet isolating agent treatment to the biological mass/organ are of special interest.

During certain cardiovascular procedures, the myocardium is flushed with cardioplegic fluid to temporarily arrest cardiac function. There are devices that are configured to selectively arrest the heart and permit cardiopulmonary bypass. These devices are aimed at collecting deoxygenated blood before it enters the heart and providing oxygen rich blood to the body without using the heart or lung. Often a venting conduit is included to eliminate all blood from the heart and decompress the chambers. Incoming blood is redirected to an oxygen-providing device, instead of passing through the heart, and then returned to the body. However, these systems are not designed for removal of potentially systemically toxic fluid that is circulating in the coronary arteries.

Still other delivery devices provide for retrograde administering of the agent against the flow of blood through the tissue. Retrograde perfusion in the heart is through the coronary veins, across the capillary beds and to the coronary arteries. A drawback of retrograde profusion is that blood flow must be ceased prior to administering the agent. Moreover, systolic blood flow carries the agent to other parts of the body.

Some systems for fluid delivery and collection have a single catheter and a switch to change between fluid delivery and drainage. One drawback to single catheter devices is that they do not permit simultaneous delivery at one site and collection of those chemicals at another site.

Thus, there is a need for a procedure to isolate the location of agent contact. The system used in such a procedure should allow for prolonged agent treatment to a site while minimizing damage to the tissue. The system should provide for optimal perfusion of a tissue. In particular, a platform for delivering and collecting fluids in the direction of the circulatory flow path of a target site would be advantageous.

SUMMARY OF THE INVENTION

A fluid isolation system is provided for confining fluid in a biological mass, which tissue has at least one upstream channel and at least one downstream channel. In one embodiment, the system comprises a delivery conduit for administering fluid to the biological mass and a collection conduit for reclaiming the fluid. The delivery conduit is positioned adjacent to or inside of the upstream channel and the collection conduit is located adjacent to or inside of the downstream channel. The conduits contain at least one lumen and often three lumens.

The biological mass that benefits from the isolation system may be any organ or tissue, including a heart. In one instance, the delivery conduit is positioned in the aorta of the heart, usually at a location close to the opening of the left and right coronary arteries and the collection conduit is situated in the coronary sinus.

The system may also be used in a biological mass having at least two upstream channels and at least one downstream channel. Some systems employed with multiple channels may have more than one delivery and/or collection conduits, where each conduit is inserted in separate channels. For example, in a heart, one delivery catheter may be positioned in the left main coronary artery and the second delivery conduit may be positioned in the right coronary artery.

The fluid transported by the isolation system frequently includes an agent. The agent may be any molecule and in some embodiments are selected from the group consisting of natural and synthetic drugs, growth factors, gene therapy compositions, chemotherapeutic chemicals, anti-bacterial chemicals, anti-angiogenesis chemicals, and any combination thereof. Usually the upstream channel is for depositing the agent to the biological mass and the downstream channel is for carrying the agent from the biological mass.

The collection conduit has a collection seal for occluding fluid flow outside of the conduit, e.g. fluid flowing downstream to any other biological mass. A delivery seal, such as an elastomeric balloon, is optionally present on the exterior of the delivery conduit to occlude fluid from flowing outside of the delivery catheter, for example, fluid is prevented from flowing in an upstream direction to other biological masses. The seals may be activated and deactivated, e.g. contracted and expanded, by a control mechanism. The seals may be configured for use in a heart where the seal is expanded during at least a substantial period of diastole and contracted during at least a substantial period of systole. In still another embodiment, the collection catheter and/or delivery catheter also may have an internal collection seal. The benefits of all of these seals are direct in that the route of fluid flow external and internal to the conduits may be selectively controlled.

In still other cases, the system further includes a driving and/or drainage force to encourage fluid movement through the delivery conduit and/or collection conduit. These forces may be timed to govern when fluid movement occurs and the rate of flow. For example, the rhythm of the driving and/or drainage forces may be regulated in conjunction with seal activation and deactivation or with the natural pulse of blood flow through the channels.

Fluid delivery into the heart may be regulated to correspond with the natural rhythm of the heart. In one example, fluid is delivered only during diastole. In another method of operation, fluid is delivered constantly during diastole and systole periods, where during systole, the delivery seal is contracted and fluid is made to flow with the natural blood flow through the heart.

A system is also provided having the fluid for flowing through an upstream channel and downstream channel of the biological mass, a delivery conduit for administering the fluid to the upstream channel and a collection conduit having an external seal for acquiring the fluid from the downstream channel. In other embodiments of a system, a second delivery conduit is additionally included. In still further embodiments, the system comprises an agent for combination with the fluid and for transport to the biological mass via the upstream and downstream channels, as well as the delivery and collection conduits.

In addition, the present invention includes methods of using the various embodiments of fluid isolation system described above. In one method of use, a delivery conduit is inserted adjacent to or inside of an upstream channel of the biological mass and a collection conduit having an external seal is inserted adjacent to or inside of a downstream channel of the biological mass. The external seal is activated to occlude fluid flow outside of the collection conduit. Fluid is delivered through the delivery conduit to the upstream channel and allowed to flow into the downstream channel and into the collection conduit.

The present invention finds use in many applications where local treatment with fluid is required. The invention is especially valuable where multiple treatment sites are spread throughout a tissue, e.g. organ. The fluid flowing through the tissue's circulatory pathway may contact and treat these dispersed target sites. The fluid is thereafter collected and prevented from reaching other areas of the body.

A further use of the fluid isolation system, according to the present invention, is in lengthy treatment protocols. The system may be adapted to continuously infuse fluid through a tissue over a long period of time, e.g. several hours or days, or provide intermittent treatment with fluid. In other cases, the system may be configured to conveniently prolong the residence time of the fluid and/or agent in the tissue.

By confining the treatment area, the present invention may increase the efficacy of certain agents through limiting undesirable effects, e.g. side effects and decentralized effects, normally induced by agent contact outside of the target tissue. With use of the invention, a high concentration of agent may also be administered to the treatment area for a prolonged period of time.

Other features and advantages of these and other embodiments are discussed in detail below.

BRIEF DESCRIPTION OF THE DRAWINGS

The present invention is illustrated by way of example, and not limitation, in the figures of the accompanying drawings in which:

FIG. 1A shows an anterior view and FIG. 1B shows a posterior view.

FIGS. 3A-3B illustrates one embodiment of a collection catheter in accordance with the teachings presented herein, wherein FIG. 3A shows a side view of the collection catheter and FIG. 3B shows a cross sectional view of the catheter through the balloon end.

FIGS. 4A-4B illustrate one embodiment of a delivery catheter in accordance with the teachings presented herein, wherein FIG. 4A shows a side view of the catheter and FIG. 4B shows a cross sectional view of the catheter through the balloon end.

FIG. 5B shows one delivery catheter in the right coronary artery and another delivery catheter in the left anterior descending artery.

DETAILED DESCRIPTION

A fluid isolation system and method of its use are provided for confining fluid treatment to a target tissue. The apparatus of the present invention utilizes upstream and downstream conduits that are positioned to allow the fluid to flow along the tissue's circulatory pathway. In the method in accordance to the present invention, fluid is delivered through a conduit, flushes the tissue and thereafter is captured by another conduit.

The fluid that is transported via the present invention is any liquid or gas of interest. Exemplary fluids are water, saline, blood, plasma, etc. The fluid often contains an agent to assist in diagnosis, therapy and disease prevention. The agent may be natural and synthetic drugs, growth factors, gene therapy compositions, anti-angiogenesis chemicals, chemotherapeutic chemicals, anti-bacterial chemicals, ions, cells, small and large molecules, other agents, and any combination thereof. In particular uses, the agent may be an anti-proliferative drug for inhibiting cell proliferation, e.g. antibiotics, anti-metabolites, cytotoxic agents, steroids, hormones, anti-parasitic, anti-platelet, anticoagulants, calcium channel blockers, antihyperlipermics, alpha receptor blockers, anti-connective tissue agents, anti-smooth muscle agents, and endothelial growth stimulators. In other specific applications the agent is a vector containing DNA capable of expressing a therapeutically or diagnostically useful protein, such as the gene therapy agent described in U.S. Pat. No. 5,797,870. The aforementioned agents are by way of example and are not intended to limit the choices of fluid and agent that are or may become available in the art.

Although the figures and description below shows the present invention in a human heart, the present invention may be used in other biological masses and species. The system may be applicable to any human or animal requiring fluid treatment. Essentially any tissue having accessible upstream and downstream channels is included in the intended definition of the term, "biological mass" according to the present invention, wherein the channels may be either in the tissue or proximal to the tissue and in fluid communication with the tissue. Suitable organs include kidneys, stomach, liver, brain, etc., and any combination thereof. The biological mass may also comprise a portion of an organ, for example the cortex area or medulla section of a kidney. The term biological mass is also intended to encompass specific regions of organized cells, such as areas of the skin, joints, muscles, bones, etc. One skilled in the art would adjust specific aspects of the present invention for the particular subject and biological mass of interest.

Figure 1A:
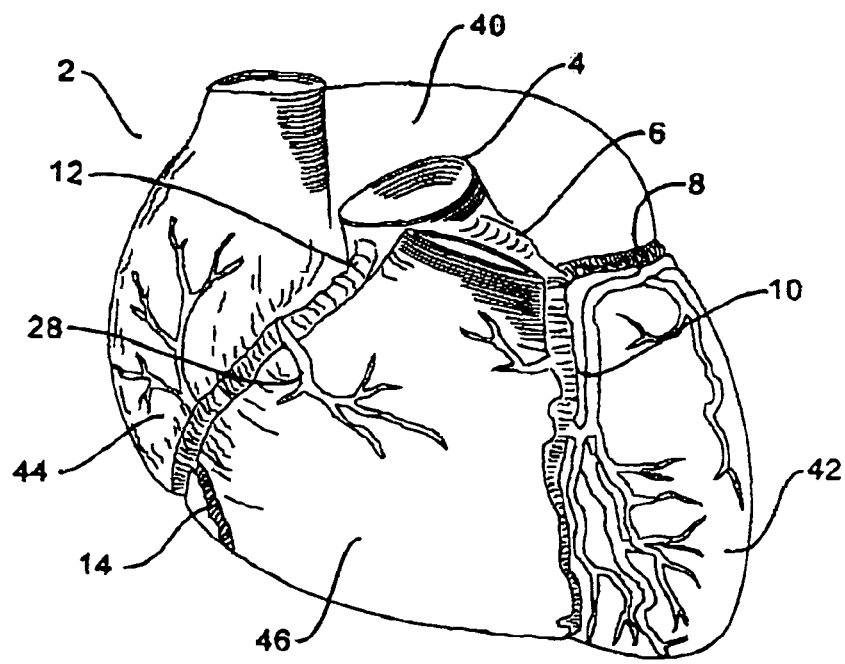
FIG. 1A-1B illustrates the circulatory system of the human heart, where
Figure 1B:
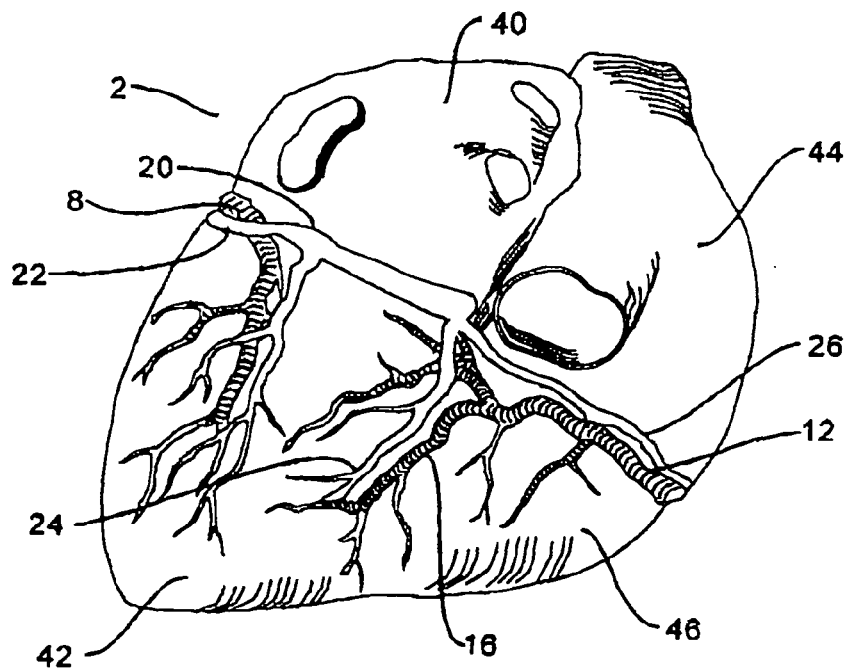

The circulatory pathway of the human heart includes coronary arterial and venous systems, as shown in FIG. 1A by an anterior view of the heart and FIG. 1B by a posterior view of the heart. The heart 2 consists of four chambers: left atrium 40, left ventricle 42, right atrium 44 and right ventricle 46. The heart 2 is nourished by the left main coronary artery 6 and right coronary artery 12 emanating from the aorta 4 at a point slightly above the semilunar valve (not shown). The left coronary artery 6 has circumflex branch 8 and anterior descending branch 10 and the right coronary artery 12 has marginal branch 14 and posterior interventricular branch 16.

The venous system comprises coronary sinus 20 that provides drainage for great cardiac vein 22, middle cardiac vein 24 and small cardiac vein 26. Fluid from the coronary sinus 20 exits through the coronary ostium (not shown) and into the right atrium 44. The venous system further includes anterior cardiac veins 28 that drain directly into the right atrium. Most of the circulating fluid in the heart drains through the coronary sinus and a very small portion of the fluid drains into the left and right atria and ventricles via the lymphatic system and the Thebesian veins.

Figure 2:
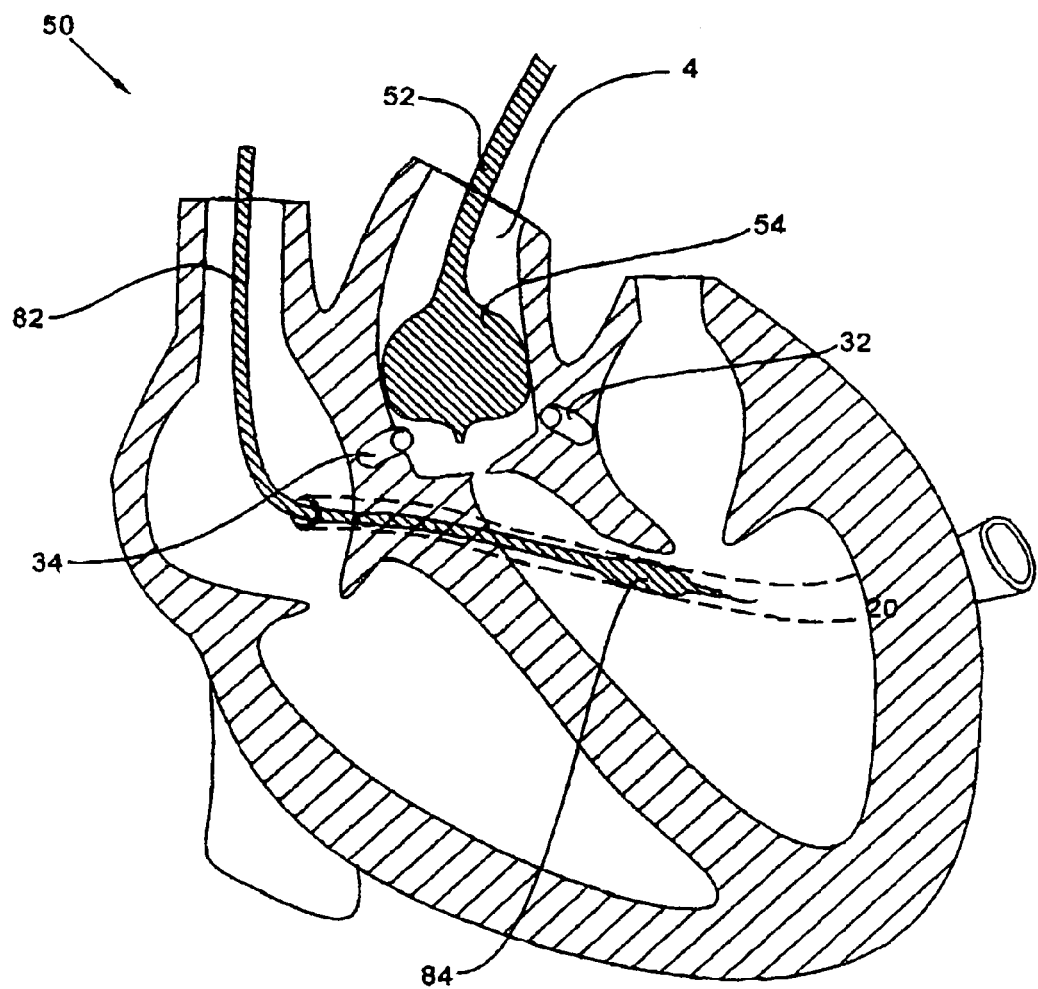
FIG. 2 illustrates one embodiment of a fluid isolation system inserted in a human heart in accordance with the teachings presented herein.

FIG. 2 depicts an exemplary fluid isolation system 50 configured in accordance with one embodiment of the present invention in a human heart to perfuse the myocardium and confine the fluid to the heart. A delivery catheter 52 is present in the aorta 4 at a position above the left aortic sinus 32 and right aortic sinus 34. Delivery catheter 52 optionally includes an external balloon seal 54. Collection catheter 82 is disposed in the central area of the coronary sinus 20 and also includes an external balloon seal 84.

For illustration purposes, FIG. 2 shows one arrangement of conduits in specific channels. Upon review of this specification, it will be appreciated by those skilled in the art that other points along the channels may be chosen for placement of the conduits, in addition to those described and shown above. In general, the location of the delivery conduit is inside of or adjacent to an upstream channel and the position of the collection conduit is inside of or adjacent to a downstream channel. Where the delivery conduit is adjacent to the channel, it is in fluid communication with the channel and should be placed close enough to the channel to allow most of the fluid to flow into the channel, rather than flowing to other parts of the body. Likewise, where the collection conduit is located adjacent to the channel, it is in fluid communication with the channel and should be close enough to the channel to gather most of the fluid from the channel.

By way of example where a delivery conduit is inside of the aorta of a heart, the delivery catheter is typically situated close to the left and right aortic ostia (openings to the coronary arteries). In this example, the delivery conduit is considered to be in a position adjacent to the upstream channels of the heart, e.g. coronary arteries. The chosen position for the collection conduit is often at a location that permits collection of circulating fluid from most or all of the tributary veins and prevents fluid from flowing into the right atrium. Thus, where the collection conduit is in the coronary sinus, the conduit is positioned downstream from where the veins meet the coronary sinus and before the coronary ostium.

The scope of the present invention also anticipates other channels in various organs that are capable of receiving a conduit. An upstream channel, e.g. vessel, sinus or artery, is a passageway for an incoming fluid stream to the biological mass and typically supplies nutrients to the mass. Thus, where the fluid contains an agent, the upstream channel usually directs the agent into the biological mass, i.e. target tissue, for deposition in the biological mass. Likewise, a downstream channel, e.g. vessel, sinus or vein, usually directs the stream flowing out of the same mass and may remove waste and excess nutrients from the mass. Where the fluid has an agent, the downstream channel carries away the undeposited and reabsorbed agent, i.e. agent absorbed by the mass and thereafter released from the biological mass. The upstream and downstream channels are in fluid communication with each other. Some preferred channels are responsible for much of the fluid flowing into or out from the organ. Channels that direct at least 70% of the in or out flowing fluid are preferred and especially channels for more than 90% of fluid flow.

Figure 3A:
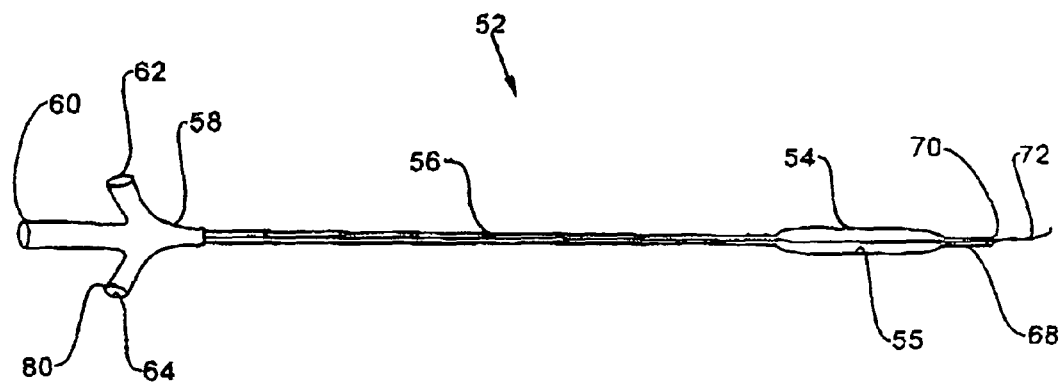
Figure 3B:
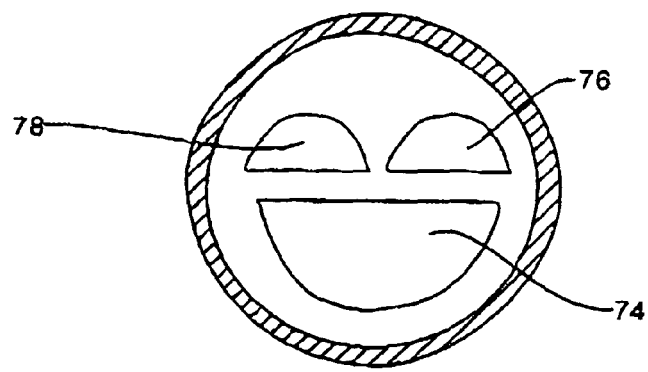

The details of one exemplary delivery catheter are illustrated in FIGS. 3A and 3B. FIG. 3A shows an elongated catheter shaft 56 having a terminal end 68 and control end 58. The control end 58 has a pressure attachment 62, i.e. port for inflating the seal, guide wire port 60 and fluid source opening 64. In an alternative embodiment the guide wire insertion opening is located distal to the pressure attachment 62. A balloon 54 is positioned proximal to the terminal end 68 of the catheter and is adapted to expand and engage an external wall with fluid tight seal. In this manner, the injected fluid is prevented from escaping through the channel and flowing away from the target tissue. One or multiple delivery openings 70 are located on the balloon for ejecting fluid into the walls of the channel. A typical PTCA guide wire 72 is used to access the site for therapy. The catheter 52 glides over the guide wire until it reaches the target site.

The diameter and shape of the terminal end 68 depends, among other factors, on the internal form and size of the channel into which the catheter is inserted. Exemplary terminal diameters range from 0.4 mm to 3.0 mm. The terminal end may conveniently include a tapered tip of various lengths, e.g. 1-6 mm. The length of the shaft depends on the length of the channel in which the catheter is introduced and typically is between about 120 cm and 150 cm. The shaft may be made of any conventional biocompatible material, e.g. a polymer or metal. The shaft may be coated with a material that assists in the use of the present invention. For example, a hydrophilic coating (Hydrocoat™ and Microglide®, both from Guidant Corporation located in Santa Clara, Calif.) provides for low friction crossing.

The balloon 54 is sized to expand and contact an external surface, such as vessel walls, and thereby occlude fluid flow. In one embodiment, the balloon is 5.0 mm to 20.0 mm in length and inflates to a diameter of 1.0 mm to 10.0 mm. The elastomeric material comprising the balloon should allow for sufficient expansion under pressure to create a seal against the external walls. Exemplary materials include polyurethanes, polyanides, polyolefines and copolymers of these families.

In addition to the elastomeric balloon, other types of expandable or mechanical seals are possible to bias against the external walls of the channel and prevent the flow of fluid external to the conduit. The expandable structure may be a meshed frame that may enlarge and contract. In another case, the conduit shaft is made to expand and press against the walls.

As shown in the cross-sectional view of a point between the control and terminal ends in FIG. 3B, one embodiment of catheter shaft 56 includes three internal lumens: a balloon inflation lumen 76, guide wire lumen 74 and drug delivery lumen 78. The diameter of each lumen depends on many factors, such as the channel in which the catheter is introduced. Various other arrangements of lumens may be found in additional suitable conduits. The diameter of the balloon inflation lumen is typically between about 0.1 and 1.0 mm, the drug delivery lumen about 0.5 and 3.0 mm and the guide wire lumen about 0.2 and 1.0 mm.

Referring again to FIG. 3A, the balloon inflation lumen 76 is in fluid communication with the interior of balloon 55 at the terminal end and pressure attachment 62 at the control end, for providing pressure to the balloon. The drug delivery lumen 78 is in fluid communication with delivery openings 70 at the terminal end and fluid source opening 64 at the control end, for delivering fluid to the tissue. The fluid source opening 64 includes a fluid attachment 80 for coupling to a fluid source. The guide wire lumen 74 communicates with the guide wire port 60, to contain a guide wire that extends through the shaft to the terminal end. Multi-lumen dilation catheters of these kinds are readily available from suppliers, such as rapid exchange (Rx) dilation catheters, perfusion catheters, and over-the-wire catheters.

Figure 4A:
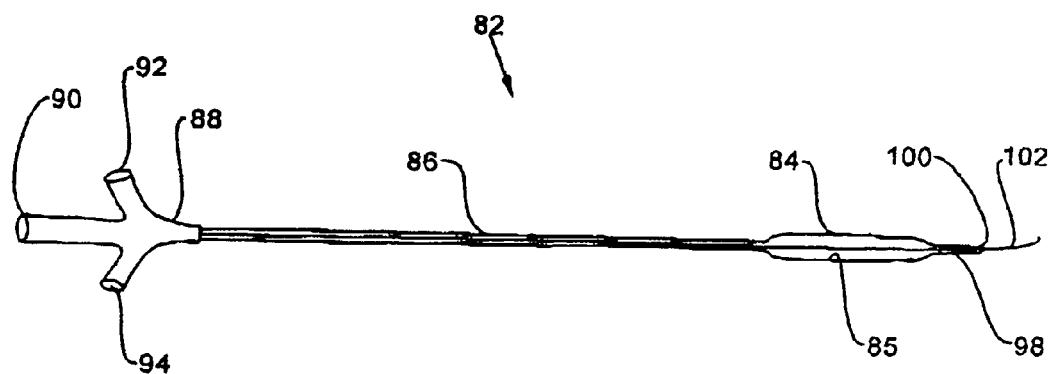
Figure 4B:
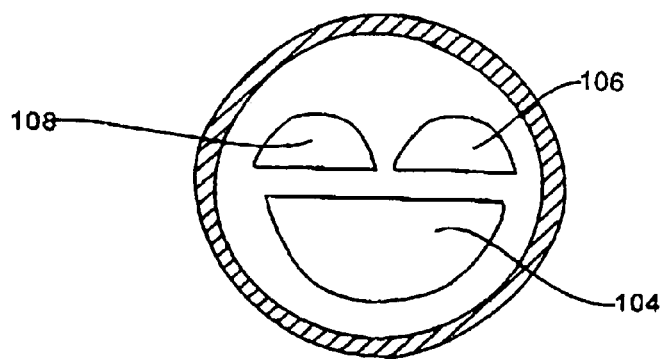

The details of the one embodiment of collection catheter are illustrated in FIGS. 4A and 4B. Typically, the collection catheter 82, as shown in FIG. 4A, is similar to the delivery catheter described above in structure, dimensions and material. The collection catheter has a shaft 86 with control end 88 and terminal end 98. Analogous to the delivery catheter, the collection catheter 82 has both a drainage opening 94 and an optional pressure attachment 92 at the control end 88 as well as a guide wire port 90 at or proximal to the control end 88. As with the delivery catheter, a seal, e.g. balloon 84, is positioned proximal the terminal end 98 and optionally a guide wire protrusion 102. In other embodiments, the seal may be any appropriate seal to occlude fluid flow and may be capable of expansion and deflation. The terminal end 98 of the catheter includes one or multiple collection ports 100 dispersed throughout the balloon for receiving fluid as well as other components flowing in the fluid stream, such as floating plaque. However, in other embodiments, the collection port may be located in various points at or proximal to the terminal end.

Further to the collection catheter represented in FIG. 4B, a drainage lumen 108 is in fluid communication with the drainage opening 94 at the control end 88 and the collection ports 100 at the terminal end 98. In some embodiments, a drainage pressure is applied to the opening through the drainage lumen. Guide wire lumen 104 communicates with the guide wire port 90 and balloon inflation lumen 106 is in fluid communication with the interior of balloon 85 at the terminal end and pressure attachment 92 at the control end, for providing pressure to the balloon.

The conduits that may be useful in the present invention may be variations of the catheters described above that are known or will be developed in the art, e.g. standard angioplasty catheters. Both the delivery and collection conduits are sized and shaped to fit inside of the appropriate area of a body and the collection conduit has an external seal.

In alternative embodiments of fluid isolation systems, different types of delivery and collection devices may be used and embodied in a variety of ways. Various conduits use mechanical forces to inject or collect fluid. For example, microporous balloon catheter (for example, Microfuse by Cortrak Medical, Inc., located in St. Paul, Minn.) and needle catheter (such as Infiltrator by Interventional Technologies, located in San Diego, Calif.) may be employed. Some delivery devices use passive diffusion to administer material. Passive conduits include double balloon catheters, spiral balloon catheters, hydrogel-coated balloon, and the like. Furthermore, a combination of driving forces, such as microneedles on balloons and microporous balloons with phonophoresis elements, etc.

The fluid may be ejected from the surface or tip of terminal end of the conduit. The agent may be positioned on a balloon and carried into the tissue by the out-flowing fluid, for example the catheter described in U.S. Pat. No. 5,180,366. In addition, the fluid may be administered by spraying, extruding or otherwise internally delivering the material by a tubular device having a single lumen or multiple lumens.

The number of lumens in the conduit may vary. One lumen may be present and accommodate the guide wire, the stream of fluid being collected or delivered, and optionally pressure. In other embodiments, the guide wire and fluid are carried in one lumen and a second lumen is used to apply pressure.

The present invention anticipates still other delivery and collection conduits. All of the aforementioned conduits are by way of example, and are not intended to limit the choices that are or may become available in the art.

Certain optional features of the collection catheter and delivery catheter are internal deployable seals. These seals may be any convenient mechanism for blocking fluid flow, such as an elastomeric balloon as described above, membrane, clamp, etc. Activation of the internal seals controls the direction of fluid flow either into the conduit, i.e. by internal seal activation. When both the internal and external seals are activated, the collection catheter blocks all fluid movement passed the location of the seals. Such impedance of fluid flow may be useful for the incubation of fluid in the target tissue for a period of time and prolonging residence time of the fluid and/or agent, permitting saturation of the tissue, and other purposes. In one case, the delivery internal seal may be activated where treatment is intermittent to block the conduit between fluid injections.

Some optional components to the fluid isolation system are mechanisms for imposing driving and/or drainage forces to the conduits to encourage or discourage fluid movement and rate of flow. Usually the driving force is positive pressure and drainage force is negative pressure. Pressure devices include positive displacement pumps, syringes, vacuums pumps, and the like. The pressure device may be a separate apparatus that is coupled to the conduit or an integral part of the conduit. In an exemplary pressure devices, a delivery pump provides positive pressure to the delivery catheter and a suction pump applies negative pressure to the collection catheter.

The delivery pump may be any conventional pump, e.g. metering pump. In one embodiment, the delivery pump is configured to provide intermittent positive pressure through the conduit. The pump may be timed to the cardiac cycle (generally synchronized with an ECG output for a patient).

In one case, the pump is configured to provide counter-pulsation with the rhythm of the heart. During at least a substantial period of diastole, i.e. majority (over half) or all of time that the heart is in diastole, pressure is applied through a lumen of the conduit, the balloon is inflated and fluid is injected from the conduit. Balloon inflation often occurs immediately following aortic valve closure during diastole. During at least a substantial period of systole, i.e. most (over half) or all of the time that the heart is in systole, the pump ceases to provide pressure, the balloon temporarily deflates and fluid injection stops. Usually pressure is stopped at the end of diastole, immediately before left ventricular contraction and systole. This counter-pulsation method is especially useful in a conduit system such as shown in FIG. 2, where the delivery conduit is in communication with a channel, e.g. the aorta, for blood flowing away from the biological mass, e.g. the heart. In this manner, delivered fluid is prevented from flowing with the blood circulating away from the biological mass during systole because fluid is only introduced during diastole. The pumping of pressure continues in this manner with each diastole and systole.

In another case, the pump is configured to constantly introduce fluid to the biological mass. Thus, fluid delivery occurs during diastole and systole periods. Furthermore, where a delivery seal is present on the delivery conduit, the seal may be inflated during diastole and contracted during systole. A continuously pumping conduit system may be of special interest where the delivery conduit is positioned directly in a channel for blood flowing into the biological mass. For example, FIGS. 5A and 5B (described in detail below) show an exemplary conduit system where the delivery conduits are located in the coronary arteries.

An exemplary delivery pump is similar to an intra-aortic balloon pump (IABP) that has known use in other medical applications to assist in the pumping of blood through the body by augmenting diastolic aortic pressure (from Datascope, located in Montvale, N.J. and from Global Medical Instrumentation, Inc. located in St. Paul, Minn.).

Moreover, other forces to encourage fluid movement and rate of flow besides pressure is within the intended scope of the present invention. For example, by positioning the control end of the conduit below the terminal end, gravity may be used to facilitate drainage. Similarly, if the control end of the conduit is above the terminal end, fluid delivery is promoted. In other embodiments, no drawing force is employed. For example, the forward pressure of fluid flowing from the delivery conduit and through the coronary circulation may be sufficient for fluid to flow into the collection conduit.

Exemplary procedures of using the fluid isolation system are described. As will be apparent to one of skill in the art of cardiology, the method represented below may be practiced with other instruments and techniques that are per se known.

To set up a fluid isolation system, the patient is prepared according to conventional procedures known in the art, usually by receiving anesthesia and optionally heparin to hinder blood clotting. The delivery catheter is percutaneously inserted into either the femoral artery or radial artery and advanced into the descending thoracic aorta. In one embodiment, the catheter remains in the aorta. In other embodiments, the delivery catheter is pushed further either into the left main coronary artery, left anterior descending artery or right coronary artery. Where two delivery catheters are employed, one of each catheter is placed into the right and left coronary arteries. The collection catheter is percutaneously introduced into the jugular vein and maneuvered into the right atrium, through the coronary ostium and into the coronary sinus.

Care must be taken while inserting the catheters that the vessels do not dissect or perforate. Furthermore, the inserting vessels must not become obstructed, potentially resulting in conditions including peripheral ischemia, systemic infection, thrombocytopenia, hemorrage and hemolysis.

With the fluid isolation system in place, fluid is made to flow through the coronary circulatory system and the heart is flushed with the fluid. The volume of fluid is chosen for the particular application of the system. The fluid is collected at the end of the circulatory pathway to prevent fluid contact with other tissues.

In one exemplary use, the balloon on the collection catheter is inflated to occlude fluid flow external to the catheter and in this manner fluid flow is diverted into the catheter. A slight drainage pressure is applied to the drainage lumen of the collection catheter to further encourage outflow through the collection catheter. The pressure should generally be sufficient to induce steady fluid flow without damage to the channel. Typical pressure amounts for the delivery catheter is between about 1.0 and 20.0 ATM and more usually about 1 ATM.

The balloon on the collection catheter is usually inflated before the delivery catheter is in place, but the delivery balloon may be expanded at the same time as the collection balloon. Typical inflation pressure is between about 3.0 and 20.0 ATM and more usually about 5.0 and 15.0 ATM. During diastole a predetermined amount of fluid is injected through the delivery lumen and out the fluid opening. Typically, the fluid source opening is attached to a metering pump to control fluid injection. Fluid flow rates are usually between 0.5 and 45 ml/min and more usually 0.5 to 15.0 ml/min. Adjustments are made to the flow rate by the attending medical practitioner with consideration of other treatment parameters.

Where a counter-pulsation pump is employed, the balloon is deflated before systole and fluid delivery is stopped. Afterwards, with the return of diastole, application of positive pressure may be resumed. This process may be repeated one or more times during the treatment until delivery of fluid is complete.

The delivery and collection procedure may be continued for any required length of time. Increased fluid absorption into the treatment site is made possible by performing a procedure for long periods of time, e.g. several hours to many days and usually about 24 hours. In further embodiments, the external seal on the collection catheter is activated to occlude outside fluid movement and the collection catheter is delayed or slowed in drainage of fluid. An internal seal may be present in the collection catheter and activated to also occlude fluid from flowing through the collection catheter. In this manner, fluid is retained in the biological mass for longer periods of time, thus prolonging residence time of the agent at the target site.

Alternatively, the delivery and collection process may be performed for a period of time and then paused for a period of time. During the pause period, the external seals may be deflated to permit external fluid flow. Where internal seals are present, the internal seals may be activated during rest. With the catheters remaining in place, the isolation process may then be proceeded again. In this manner, the catheters need not be reinserted and risk additional damage to the body.

Figure 5A:
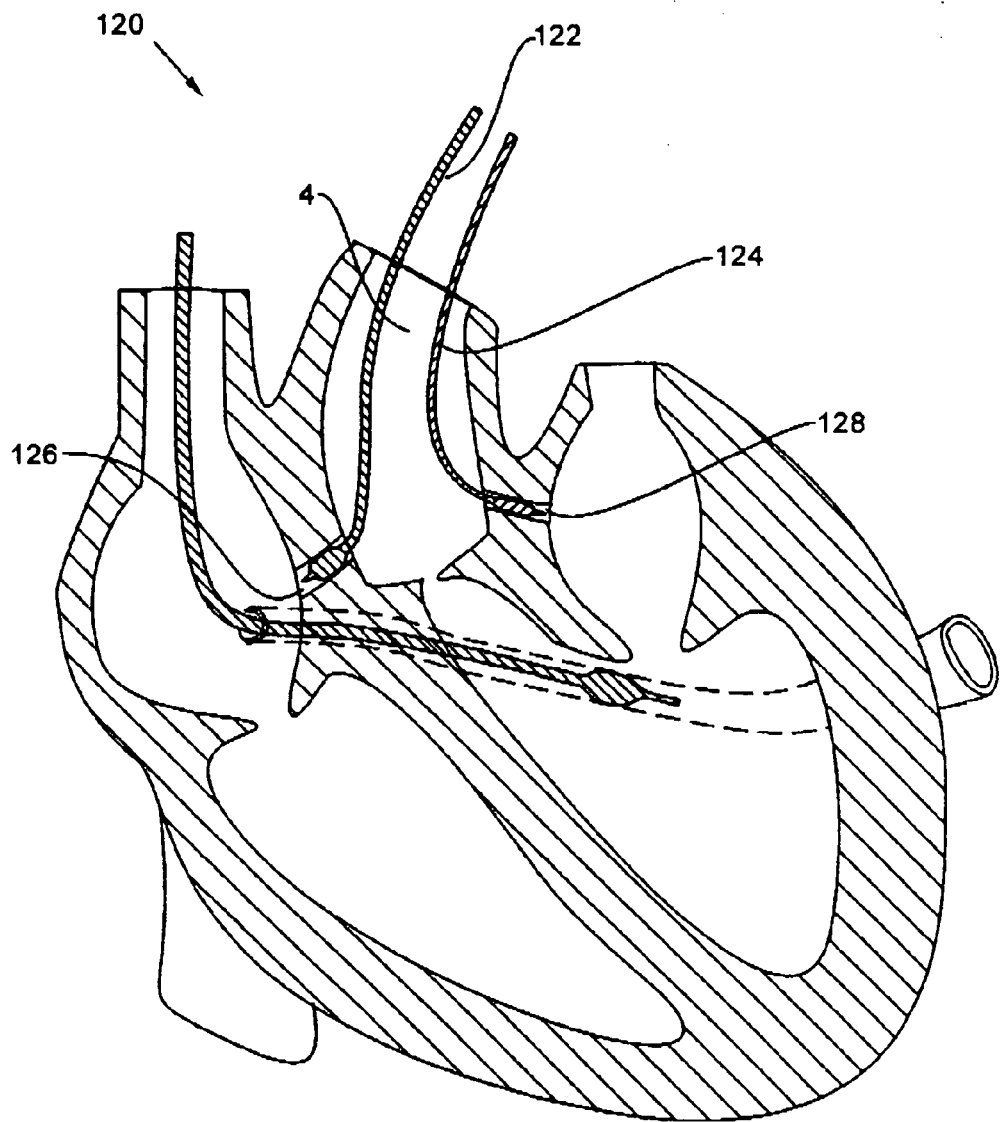
FIGS. 5A-5B illustrate various alternative embodiments of fluid isolation systems in a human heart, wherein in FIG. 5A shows two delivery catheters respectively inserted in the right coronary artery and left main coronary artery
Figure 5B:
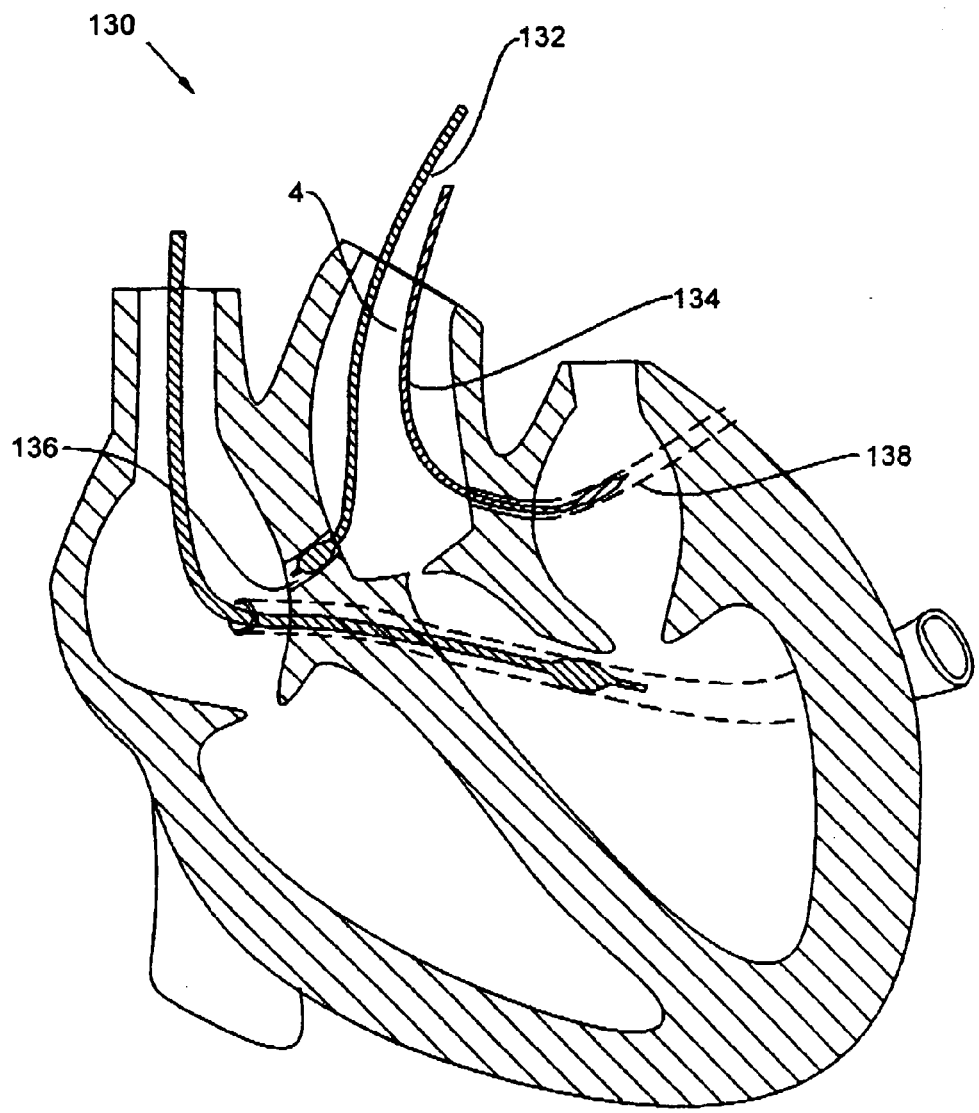

There are many alternative configurations of the fluid isolation system. In cases in which a biological mass includes multiple, e.g. two, upstream channels and/or downstream channels, the fluid isolation system includes multiple, e.g. two delivery conduits and/or collection conduits positioned in separate channels. As shown variously in FIGS. 5A to 5B, two delivery catheters are arranged in two upstream channels. Referring to FIG. 5A, fluid isolation system 120 has delivery catheters 122 and 124 that extend from the aorta 4 and are respectively inserted into both the right coronary artery 126 and the left main coronary artery 128. Both catheters may be initiated from the same channel or from separate channels, e.g. femoral and radial arteries. In another variation of fluid isolation system 130 as shown in FIG. 5B, one delivery catheter 134 is advanced through the aorta 4 into the left anterior descending artery 138 and another delivery catheter 132 is furthered through the aorta 4 and is disposed in the right coronary artery 136.

Figure 6:
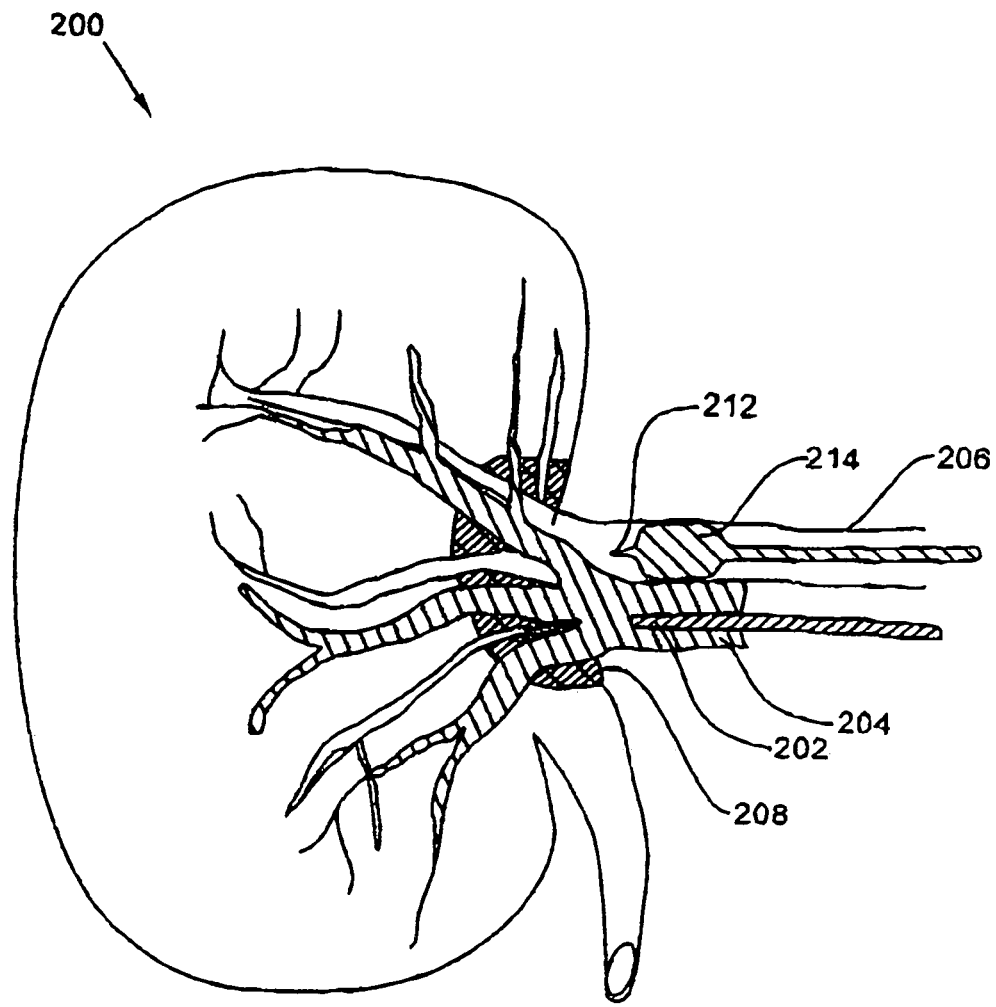
FIG. 6 illustrates of one embodiment of a fluid isolation system inserted in a human kidney and configured in accordance with the teachings presented below.

FIG. 6 illustrates another embodiment of a fluid isolation system 200 configured to localize fluid in a human kidney in accordance with the teachings presented below. The delivery catheter 202 is inserted into the right or left renal artery 204 at a location prior to branching of the arteries at the renal sinus 208. The collection catheter 212 is inserted into either the right or left renal vein 206 that corresponds to the delivery catheter placement. The collection catheter 212 is advanced to a position before the vein branches in the renal sinus. The balloon 214 on the collection catheter 212 is made to expand to occlude fluid through the vessel leading from the kidney. The process of delivering and collecting fluid is performed in the manner previously described for the heart.

The present invention has been described above in varied detail by reference to the particular embodiments and figures. However, these specifics should not be construed as limitations on the scope of the invention, but merely as illustrations of some of the presently preferred embodiments. It is to be further understood that other modifications or substitutions may be made to the described information transfer system as well as methods of its use without departing from the broad scope of the invention. Therefore, the following claims and their legal equivalents should be used to determine the scope of the invention.

What is claimed is:

1. A system for fluid isolation in a biological mass having at least one upstream channel and at least one downstream channel, comprising:
    a delivery conduit for administering a fluid to the biological mass, the delivery conduit having a length dimension suitable to be positioned from a first externally accessible channel of a patient adjacent to or into at least one upstream channel of the biological mass by way of a percutaneous transluminal route; and
    a collection conduit for acquiring the administered fluid, the collection conduit having a length dimension suitable to be positioned from a second externally accessible channel of a patient adjacent to or into at least one downstream channel of the biological mass by way of a percutaneous transluminal route and having a collection seal having a dimension, in one configuration, to occlude the at least one downstream channel;
    wherein the biological mass is selected from the group consisting of a heart, a portion of a heart, a kidney, a portion of a kidney, a stomach, a liver, and a brain.

2. The system of claim 1, further including a driving force in communication with the delivery conduit for encouraging fluid through the delivery conduit.

3. The system of claim 1, wherein the delivery conduit is for administering fluid during at least a substantial period of diastole.

4. The system of claim 1, wherein the delivery conduit is for administering fluid during the period of diastole and the period of systole.

5. The system of claim 1 wherein the delivery conduit further includes a delivery seal having a dimension, in one configuration, to occlude the at least one upstream channel and the delivery conduit defines a delivery opening distal to the delivery seal.

6. The system of claim 5 wherein the delivery seal is an elastomeric balloon.

7. The system of claim 6, wherein, in another configuration, the delivery seat allows fluid flow past the delivery seal.

8. The system of claim 7, further including a seal control mechanism for contracting and expanding the delivery seal.

9. The system of claim 8, wherein the seal control mechanism is configured to expand the delivery seal during at least a substantial period of diastole and contract the delivery seal during at least a substantial period of systole.

10. The system of claim 1, wherein the biological mass is a human heart.

11. The system of claim 1, wherein the delivery conduit is such that the delivery conduit may be positioned into an aorta of a patient and the length dimension of the collection conduit is such that the collection conduit may be positioned into a coronary sinus of the patient.

12. The system of claim 1, wherein the fluid includes an agent.

13. The system of claim 12, wherein the agent is selected from the group consisting of natural and synthetic drugs, growth factors, gene therapy compositions, chemotherapeutic chemicals, anti-bacterial chemicals, anti-angiogenic chemicals and any combination thereof.

14. The system of claim 1, wherein the first externally accessible channel is selected from one of a femoral artery and a radial artery.

15. The system of claim 14, wherein the second externally accessible channel is a jugular vein.

16. A system comprising:
    a delivery conduit having a length dimension suitable to be positioned by a percutaneous transluminal route from a first externally accessible channel of a patient adjacent to or into an upstream channel of a biological mass selected from the group consisting of a heart, a portion of a heart, a kidney, a portion of a kidney, a stomach, a liver, and a brain, and where the biological mass comprises at least one upstream channel and at least one downstream channel;
    a separate collection conduit having a dimension suitable to be positioned by a percutaneous transluminal route from a second externally accessible channel of a patient adjacent to or into a downstream channel of the biological mass, the separate collection conduit comprising a collection seal for occluding fluid flow by the collection seal; and
    a fluid to be administered to the biological mass through the delivery conduit, and reclaimed by the collection conduit, wherein the system achieves fluid isolation in the biological mass between the upstream channel and the downstream channel has at least one upstream channel and at least one downstream channel.

17. The system of claim 16, wherein the fluid further comprises an agent.

18. The system of claim 17, wherein the agent is selected from the group consisting of natural and synthetic drugs, growth factors, gene therapy compositions, chemotherapeutic chemicals, anti-bacterial chemicals, anti-angiogenic chemicals, and combinations thereof.

19. The system of claim 16, wherein the delivery conduit further comprises a delivery seal for occluding external fluid flow.

20. The system of claim 19, wherein the delivery seal comprises an elastomeric balloon.

21. The system of claim 16, further comprising a pressure device, wherein the pressure device is in fluid communication with the delivery conduit.

22. The system of claim 21, wherein the pressure device exerts a positive pressure, and the pressure device is selected from the group consisting of positive displacement pumps, syringes, vacuum pumps, delivery pumps, suction pumps, metering pumps, and intra-aortic balloon pumps.

23. The system of claim 16, further comprising a pressure device in fluid communication with the collection conduit.

24. The system of claim 23, wherein the pressure device exerts a negative pressure, and the pressure device is selected from the group consisting of positive displacement pumps, syringes, vacuum pumps, delivery pumps, suction pumps, metering pumps, and intra-aortic balloon pumps.

25. The system of claim 16, wherein the delivery conduit comprises a delivery catheter, wherein the delivery catheter includes three internal lumens.

26. The system of claim 16, wherein the delivery conduit comprises a delivery catheter, wherein the delivery catheter comprises as separate lumens, a balloon inflation lumen, a guidewire lumen, and a drug delivery lumen.

27. The system of claim 16, wherein the separate collection conduit comprises a collection catheter, wherein the collection catheter comprises three lumens.

28. The system of claim 16, wherein the separate collection conduit comprises a collection catheter, wherein the collection catheter comprises as separate lumens, a drainage lumen, a guidewire lumen, and a balloon inflation lumen.

29. The system of claim 16, wherein the first externally accessible channel is selected from one of a femoral artery and a radial artery.

30. The system of claim 29, wherein the second externally accessible channel is a jugular vein.

\* \* \* \* \*